(12) United States Patent
Katz et al.

(10) Patent No.: US 6,344,153 B1
(45) Date of Patent: Feb. 5, 2002

(54) HELICAL DISCOTIC SWITCH

(75) Inventors: Thomas J. Katz, New York, NY (US); Colin P. Nuckolls, San Clemente, CA (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 09/384,475

(22) Filed: Aug. 27, 1999

(51) Int. Cl.[7] .......................... C09K 19/32; F21V 9/00; C07C 41/00; C07C 69/76; C09B 3/02

(52) U.S. Cl. .................... 252/299.62; 552/284; 560/73; 568/326; 568/633; 252/582

(58) Field of Search ........................ 252/299.01, 299.62, 252/582; 349/118; 552/273, 284; 568/633, 326; 560/73

(56) References Cited

U.S. PATENT DOCUMENTS

| | | | |
|---|---|---|---|
| 4,619,788 A | * 10/1986 | Zimmermann et al. | 252/299.62 |
| 5,583,679 A | * 12/1996 | Ito et al. ..................... | 349/118 |
| 5,635,105 A | * 6/1997 | Kawata et al. ......... | 252/299.01 |
| 5,718,838 A | 2/1998 | Okazaki et al. ........ | 252/299.01 |
| 6,017,470 A | * 1/2000 | Katz et al. .................. | 252/582 |
| 5,993,700 A | 11/2000 | Katz et al. .................. | 252/582 |

OTHER PUBLICATIONS

Nuckolls et al., "Aggrgation of Conjugated Helical Molecules", J. Am. Chem. Soc. 118, 5767–5768, 1996.*
Nuckolls et al., "Circular Dichroism and UV–Visible Asorption Spectra of the Langmuir–Blodgett Films of an Aggregation Helicene", J. Am. Chem. Soc. vol. 120, 8656–8660, 1998.*
PCT International Search report of International Application No. PCT/US00/23460, Dated Nov. 8, 2000 (Exhibit 1).
Barbera, J., et al., (1998) "Switchable Columnar Metallomesogens. New Helical Self–Assembling Systems", J. Am. Chem. Soc., 120: 2908–2918 (Exhibit 1).
Biscarini, F., et al., (1991) "Head–tail asymmetry ferroelectricity in uniaxial liquid crystals. Model calculations", Mol. Phys., 73: 439 (Exhibit 2).
Bock, H. and Helfrich W., (1992) "Ferroelectrically switchable columnar liquid crystal", Liq. Cryst., 12: 697 (Exhibit 3).
Bock, H. and Helfrich W., (1995) "Two ferroelectric phases of a columnar dibenzopyrene", Liq. Cryst., 18:387 (Exhibit 4).
Boden, N., et al., (1997) "α–Halogenation of triphenylene–based discotic liquid crystal: towards a chiral nucleus", J. Nater. Chem., 7: 601–605 (Exhibit 5).
Cometti, G., et al., (1990) "New Bowl–shaped Columnar Liquid Crystals", J. Chem. Soc., Chem. Commun., : 163 (Exhibit 6).

Gottarelli, G., et al., (1996) "The Self–Recognition and Self–Assembly of Folic Acid Salts in Isotropic Water Solution", Helv. Chim. Acta., 79: 220–234 (Exhibit 7).
Huang, D., et al., (1996) Synthesis of Philanthotoxin Analogs with Bulky Heads Including Porphyrins. Self–assembly Monitored by Circular Dichroism, Heterocycles, 42: 723–736 (Exhibit 8).
Jackli, A., et al., (1998) "First observation of electromechanical effects in a chiral ferroelectric columnar liquid crystal", Liq. Cryst., 24: 467–472 (Exhibit 9).
Jakli, A., et al., (1997) "Indication of ferroelectricity in columnar mesophases of pyramidic molecules", Liq. Cryst., 22: 309 (Exhibit 10).
Jeffery, G. A. and Wingert, L. M., (1992) "Invited Article: Carbohydrate Liquid Crystals", Liq. Cryst., 12: 179–202 (Exhibit 11).
Kohne, B. and Praefcke, K., (1984) "Hexa–O–alkanoyl–scyllo–inositols, the First Alicyclic, Saturated, Discotic Liquid Crystals", Angew. Chem Soc. Int. Ed. Engl.., 23:82–83 (Exhibit 12).
Levelut, A., et al., (1986) "X–ray structural study of the mesophases of some cone–shaped molecules", J. Phys., 47: 351 (Exhibit 13).
Lovinger, A. J., et al., (1998) "Structure and Morphology of Helicene Fibers", J. Am. Chem. Soc., 120: 264–268 (Exhibit 14).

(List continued on next page.)

*Primary Examiner*—Shean C. Wu
(74) *Attorney, Agent, or Firm*—John P. White; Cooper & Dunham LLP (57) ABSTRACT

The present invention provides liquid crystal having a spiral coil structure and a dipole moment along its axis and a helical discotic switch using the same, wherein the helicene compound has the structure:

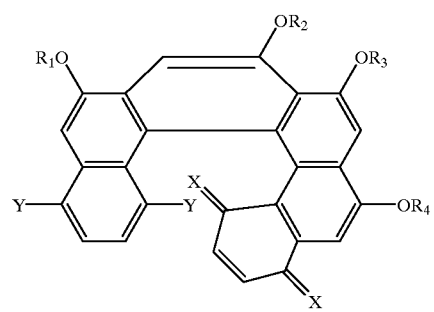

wherein X is O, or S and Y is —O—C(=O)CH$_2$—O—R$_5$, wherein R$_5$ is H, substituted or unsubstituted alkyl, alkenyl, cycloalkyl, aryl, or arylalkyl, wherein R$_1$, R$_2$, R$_3$ and R$_4$ are independently the same or different and are substituted or unsubstituted alkyl, alkenyl, cycloalkyl, aryl, or arylalkyl.

36 Claims, 8 Drawing Sheets

OTHER PUBLICATIONS

Malthete, J. and Collet, A., (1987) "Inversion of the Cyclotribenzylene Cone in a Columnar Mesophase: A Potential Way to Ferroelectric Materials", J. Am. Chem. Soc., 107: 7544–7545 (Exhibit 15).

Markovitsi, D., et al., (1995) "Triphenylene Columnar Liquid Crystals: Excited States and Energy Transfer", J. Phys. Chem., 99: 1005–1017 (Exhibit 16).

Matile, S., et al., (1996) "Exciton coupled circular dichroic studies of self–assembled brevetoxin–porphyrin conjugates in lipid bilayers and polar solvents", Chem. Biol., 3: 379–392 (Exhibit 17).

Malthete, J. and Collet, A., (1987) "Inversion of the Cyclotribenzylene Cone in a Columnar Mesophase: A Potential way to Ferroelectric Materials", J. Am. Chem. Soc., 107: 7544 (Exhibit 18).

Mukkamala, R., et al., (1998) "Photopolymerization of Carbohydrate–Based Discotic Mesogens. Syntheses and Phase Properties of 1, 2, 3, 4, 6–Penta–O–(trans–3, 4–dialkoxycinnamoyl)–(D)–glucopyranoses and Their Oligomers", J. Am. Chem. Soc., 118: 9498–9508 (Exhibit 19).

Nuckolls, C., et al., (1996) "Aggregation of Conjugated Helical Molecules", J. Am. Soc., 118: 3767–3768 (Exhibit 20).

Nuckolls, C. and Katz, T. J., (1998) "Synthesis, Structure, and Properties of a Helical Columnar Liquid Crystal", J. Am. Chem. Soc., 120: 9541–9544 (Exhibit 21).

Nuckolls, C., et al., (1998) "Synthesis, Structure, and Properties of a Helical Columnar Liquid Crystal", A. J. Am. Chem. Soc., 120(37): 9541–9544 (Exhibit 22).

Palmans, A. R. A., et al., (1978) "Lyotropic Liquid–Crystalline Behavior in Disc–Shaped Compounds Incorporating the 3,3'–Di(acylamine)–2,2'–bipyridine Unit", Adv. Mater., 10: 873 (Exhibit 23).

Piechocki, C., et al., (1987) "Discotic Mesogens Possessing an Electrical Dipole Moment Perpendicular to the Molecular Plane: Synthesis and Mesomorphic Properties", Mol. Cryst. Liq. Cryst., 149: 115 (Exhibit 24).

Praefcke, K., et al., (1987) "Core–halogenated, helical–chiral triphenylene–based columnar liquid crystals", Liq. Cryst., 22: 113–119 (Exhibit 25).

Scherowsky, G. and Chen, X. H., (1995) "Ferroelectric Switching in Columnar Phases of Novel Chiral Discotic Liquid Crystal", J. Mater. Chem., 5: 417 (Exhibit 26).

Schnur, J. M., et al., (1994) "Diacetylenic Lipid Tubules: Experimental Evidence for a Chiral Molecular Architecture", Science, 264: 945–947 (Exhibit 27).

Serrette, A. G., et al., (1994) "Complementary Shapes in Columnar Liquid Crystals: Structural Control in Homo– and Heteronuclear Bimetallic Assemblies", Chem. Mater., 6: 2252–2268 (Exhibit 28).

Serrete, A. G., et al., (1993) "Controlling Intermolecular Associations with Molecular Superstructure: Polar Discotic Linear Chain Phases", J. Am. Chem. Soc., 115: 8879 (Exhibit 29).

Serrette, A. G., et al., (1994) "Polar Superstructures Stabilized by Polimeric Oxometal Units: Columnar Liquid Crystals Based on tapered Dioxomolybdenum Complexes", Angew. Chem. Int. Ed. Eng., 33: 2342 (Exhibit 30).

Tabushi, I., et al., (1987) "Liquid crystals. 1. β–Oxygen Effect on Stabilization of Hexakis (acyloxy) benzene Mesophase", J. Org. Chem., 52: 2502–2505 (Exhibit 31).

Tabushi, I., et al., (1987) "Liquid crystals–II. The tail design via β–oxygen atom modifications for the remarkably enhanced stability of hexakis(alkanoyloxy)triphenylene mesophase", Tetrahedron Lett., 28: 2269–2272 (Exhibit 32).

Trzaska, S. T., et al., (1999) "Cooperative Chirality in Columnar Liquid Crystal: Studies of Fluxional Octahedral Metallomesogens", J. Am. Chem. Soc., 121: 4518 (Exhibit 33).

Usol'tseva, N., et al., (1994) "Modulation the spontaneous polarization of a ferroelectric liquid crystal via the photoisomerization of a chiral thioindigo dopant: (R,R)–6, 6'–bis(1–methylheptyloxy)thioindigo".

Verbiest, T., et al., (1998) "Strong Enhancement of Nonlinear Optical Properties Through Supramolecular Chirality", Science, submitted for publication (Exhibit 35).

Wang, L., et al., (1990) "Liquid crystals of bowl–like molecules", Chem. Phys., 142: 335 (Exhibit 36).

Xu, B., et al., (1993) "Rigid Bowlic Liquid Crystals Based on Tungsten–Oxo Calix [4]arenes: Host Guest Effects and Head–to–Tail Organization", J. Am. Chem. Soc., 115: 1159 (Exhibit 37).

Zheng, H., et al., (1993) "The development of polar discotic metallomesogens. Vandyl 1,3–diketonate complexes", Liq. Cryst., 14: 1421 (Exhibit 38).

Zheng, H., et al., (1995) "Controlling Intermolecular Interactions between Metallomesogens: Side Chain Effects in Discotic Copper, Palladium, and Vandyl Bis(β–Diketonates)",Chem. Mater., 7: 2067 (Exhibit 39).

Zimmermann, H., et al., (1985) "Pyramidic Mesophases", Naturforsch., A, 40a: 149 (Exhibit 40).

* cited by examiner

HELICAL DISCOTIC SWITCH

The invention disclosed herein was made with Government support under the NSF Grant No. CHE98-02316. Accordingly, the U.S. Government has certain rights in this invention.

Throughout this application, various references are referred to within parentheses. Disclosures of these publications in their entireties are hereby incorporated by reference into this application to more fully describe the state of the art to which this invention pertains. Full bibliographic citation for these references may be found at the end this application, preceding the claims.

BACKGROUND OF THE INVENTION

Nonracemic columnar liquid crystalline materials have been widely used in display devices such as those in calculators, digital watches, flat panel computer screens and flat penal televisions. Most of these nonracemic columnar liquid crystalline materials include planar discotic mesogens in which the asymmetry is in the side chains.[1-12] The only examples in which the cores are chiral are derivatives of saccharides,[13-14] inositols,[13-15] and cyclotriveratrylene.[16] Remarkably, no property of any of these latter materials' mesophases has yet been detected that is consequent on the cores' chirality. In their review in 1992,[14] Jeffrey and Wingert asserted that to their knowledge "there is no basic distinction between the mesophases formed by derivatives of a chiral molecule, such as D-glucitol, and a meso molecule, such as galactitol." This distinction appears not to have been made in the few years since that review.

While attempts have been made to synthesize mesogenic materials in which the planar aromatic cores of molecules constituting liquid crystals are twisted helically,[17-19] in part because chiral columnar liquid crystals have the capacity to undergo ferroelectric switching,[1,2,5,20] none that is nonracemic has been obtained until now. We describe below the synthesis and uses of the first, nonracemic helical columnar liquid crystal and its applications in making a helical discotic switch.

SUMMARY OF THE INVENTION

The present invention provides a helicene compound having the structure:

wherein X is O, or S and Y is —O—C(═O)CH$_2$—O—R$_5$, wherein R$_5$ is H, substituted or unsubstituted alkyl, alkenyl, cycloalkyl, aryl, or arylalkyl, wherein R$_1$, R$_2$, R$_3$ and R$_4$ are independently the same or different and are substituted or unsubstituted alkyl, alkenyl, cycloalkyl, aryl, or arylalkyl.

The present invention further provides a helicene compound wherein R$_1$, R$_2$, R$_3$ and R$_4$ are substituted or unsubstituted alkyl or aryl.

The present invention also provides liquid crystal having a spiral coil structure and a dipole moment along its axis, comprising a helicene compound having the structure:

wherein X is O, or S and Y is —O—C(═O)CH$_2$—O—R$_5$, wherein R$_5$ is H, substituted or unsubstituted alkyl, alkenyl, cycloalkyl, aryl, or arylalkyl, wherein R$_1$, R$_2$, R$_3$ and R$_4$ are independently the same or different and are substituted or unsubstituted alkyl, alkenyl, cycloalkyl, aryl, or arylalkyl; wherein the liquid crystal has the capacity to undergo ferroelectric switching.

The invention also provides a helical discotic switch comprising (a) the liquid crystal, (b) a rubbed substrate deposited with the liquid crystal having a planar orientation, and (c) electrodes for applying an electric field perpendicular to the rubbed substrate which changes the orientation of the liquid crystal, thus preventing the transmission of light.

DETAILED DESCRIPTION OF THE INVENTION

The present invention provides a helical discotic switch comprising (a) Liquid crystal having a spiral coil structure and a dipole moment along its axis, comprising a helicene compound having the structure:

wherein X is O, or S and Y is —O—C(=O)CH$_2$—O—R$_5$, wherein R$_5$ is H, substituted or unsubstituted alkyl, alkenyl, cycloalkyl, aryl, or arylalkyl, wherein R$_1$, R$_2$, R$_3$ and R$_4$ are independently the same or different and are substituted or unsubstituted alkyl, alkenyl, cycloalkyl, aryl, or arylalkyl; wherein the liquid crystal has the capacity to undergo ferroelectric switching, (b) a rubbed substrate deposited with the liquid crystal having a planar orientation, and (c) electrodes for applying an electric field perpendicular to the rubbed substrate which changes the orientation of the liquid crystal, thus preventing the transmission of light.

In one embodiment of the helical discotic switch, R$_1$, R$_2$, R$_3$ and R$_4$ are substituted or unsubstituted alkyl or aryl.

In another embodiment of the helical discotic switch, R$_1$, R$_2$, R$_3$ and R$_4$ are substituted or unsubstituted aryl.

In another embodiment of the helical discotic switch, R$_1$, R$_2$, R$_3$ and R$_4$ have the structure C$_n$H$_m$ wherein n is an integer $\geq 3$ and m is an integer $\leq 2n+1$.

In another embodiment of the helical discotic switch, R$_1$, R$_2$, R$_3$ and R$_4$ have the structure C$_n$H$_m$ wherein n is an integer from 3 to 50 and m is an integer from 7 to 101.

In another embodiment of the helical discotic switch, R$_1$, R$_2$, R$_3$ and R$_4$ have the structure C$_n$H$_m$ wherein n is an integer from 12 to 30 and m is an integer from 25 to 61.

In another embodiment of the helical discotic switch, R$_1$, R$_2$, R$_3$ and R$_4$ have the structure C$_n$H$_m$ wherein n is 12 and m is 25.

In another embodiment of the helical discotic switch, R$_1$, R$_2$, R$_3$ and R$_4$ are alkylaryl.

In another embodiment of the helical discotic switch, R$_5$ is H.

In another embodiment of the helical discotic switch, R$_5$ is substituted or unsubstituted alkyl or aryl.

In another embodiment of the helical discotic switch, R$_5$ is benzyl.

In another embodiment of the helical discotic switch, the electric field is generated by a square or a triangular electric wave.

In another embodiment of the helical discotic switch, the electric field is generated by a triangular electric wave.

In another embodiment of the helical discotic switch, the electric wave has a peak to peak voltage of at least 20 volts to generate light switching effect.

In another embodiment of the helical discotic switch, the electric wave has a peak to peak voltage 20 and 2,000 volts to generate light switching effect.

In another embodiment of the helical discotic switch, the triangular electric wave has a peak to peak voltage 30 and 1,000 volts to generate light switching effect.

In another embodiment of the helical discotic switch, the triangular electric wave has a peak to peak voltage 60 and 300 volts to generate light switching effect.

In another embodiment of the helical discotic switch, the switching time for light transmission is between 0.0001 and 0.2 seconds.

In another embodiment of the helical discotic switch, the switching time for light transmission is between 0.0005 and 0.1 second.

In another embodiment of the helical discotic switch, the switching time for light transmission is between 0.001 and 0.01 second.

In another embodiment of the helical discotic switch, the helicene compound is in an organic solvent at a concentration between 0.1 and 2 molars.

In another embodiment of the helical discotic switch, the organic solvent comprises dodecane.

In another embodiment of the helical discotic switch, the application of an eletric field to the helicene compound switches its electric conductivity.

In another embodiment of the helical discotic switch, the switching of electric conductivity is achieved by an electric field having a voltage of at least 250 volts.

In yet another embodiment of the helical discotic switch, the switching of electric conductivity is achieved by an electric field having a voltage between 250 and 2,000 volts.

In a further embodiment of the helical discotic switch, the switching of electric conductivity is achieved by an electric field having a voltage between 300 and 1,000 volts.

The present invention further provides liquid crystal having a spiral coil structure and a dipole moment along its axis, comprising a helicene compound having the structure:

wherein X is O, or S and Y is —O—C(=O)CH$_2$—O—R$_5$, wherein R$_5$ is H, substituted or unsubstituted alkyl, alkenyl, cycloalkyl, aryl, or arylalkyl, wherein R$_1$, R$_2$, R$_3$ and R$_4$ are independently the same or different and are substituted or unsubstituted alkyl, alkenyl, cycloalkyl, aryl, or arylalkyl; wherein the liquid crystal has the capacity to undergo ferroelectric switching.

In one embodiment of the liquid crystal, R$_1$, R$_2$, R$_3$ and R$_4$ are substituted or unsubstituted alkyl or aryl.

In another embodiment of the liquid crystal, R$_1$, R$_2$, R$_3$ and R$_4$ are substituted or unsubstituted aryl.

In another embodiment of the liquid crystal, $R_1$, $R_2$, $R_3$ and $R_4$ have the structure $C_nH_m$ wherein n is an integer ≧3 and m is an integer ≦2n+1.

In another embodiment of the liquid crystal, $R_1$, $R_2$, $R_3$ and $R_4$ have the structure $C_nH_m$ wherein n is an integer from 3 to 50 and m is an integer from 7 to 101.

In another embodiment of the liquid crystal, $R_1$, $R_2$, $R_3$ and $R_4$ have the structure $C_nH_m$ wherein n is an integer from 12 to 30 and m is an integer from 25 to 61.

In another embodiment of the liquid crystal, $R_1$, $R_2$, $R_3$ and $R_4$ have the structure $C_nH_m$ wherein n is 12 and m is 25.

In another embodiment of the liquid crystal, $R_1$, $R_2$, $R_3$ and $R_4$ are alkylaryl.

In another embodiment of the liquid crystal, $R_5$ is H.

In yet another embodiment of the liquid crystal, $R_5$ is substituted or unsubstituted alkyl or aryl.

In a further embodiment of the liquid crystal, $R_5$ is benzyl.

The present invention also provides a helicene compound having the structure:

wherein X is O, or S and Y is —O—C(=O)CH$_2$—O—$R_5$ wherein $R_5$ is H, substituted or unsubstituted alkyl, alkenyl, cycloalkyl, aryl, or arylalkyl, wherein $R_1$, $R_2$, $R_3$ and $R_4$ are independently the same or different and are substituted or unsubstituted alkyl, alkenyl, cycloalkyl, aryl, or arylalkyl.

In one embodiment of the helicene compound, $R_1$, $R_2$, $R_3$ and $R_4$ are substituted or unsubstituted alkyl or aryl.

In another embodiment of the helicene compound, $R_1$, $R_2$, $R_3$ and $R_4$ are substituted or unsubstituted aryl.

In another embodiment of the helicene compound, $R_1$, $R_2$, $R_3$ and $R_4$ have the structure $C_nH_m$ wherein n is an integer ≧3 and m is an integer ≦2n+1.

In another embodiment of the helicene compound, $R_1$, $R_2$, $R_3$ and $R_4$ have the structure $C_nH_m$ wherein n is an integer from 3 to 50 and m is an integer from 7 to 101.

In another embodiment of the helicene compound, $R_1$, $R_2$, $R_3$ and $R_4$ have the structure $C_nH_m$ wherein n is an integer from 12 to 30 and m is an integer from 25 to 61.

In another embodiment of the helicene compound, $R_1$, $R_2$, $R_3$ and $R_4$ have the structure $C_nH_m$ wherein n is 12 and m is 25.

In another embodiment of the helicene compound, $R_1$, $R_2$, $R_3$ and $R_4$ are alkylaryl.

In another embodiment of the helicene compound, $R_5$ is H.

In yet another embodiment of the helicene compound, $R_5$ is substituted or unsubstituted alkyl or aryl.

In a further embodiment of the helicene compound, $R_5$ is benzyl.

This invention further provides a liquid crystal having a spiral coil structure and a dipole moment along its axis, comprising the helicene compound having the structure:
wherein X is O, or S and Y is —O—C(=O)CH$_2$—O—$R_5$, wherein $R_5$ is H, substituted or unsubstituted alkyl, alkenyl, cycloalkyl, aryl, or arylalkyl, wherein $R_1$, $R_2$, $R_3$ and $R_4$ are independently the same or different and are substituted or unsubstituted alkyl, alkenyl, cycloalkyl, aryl, or arylalkyl.

In one embodiment of the liquid crystal, the helicene compound has the structure:

wherein X is O, or S and Y is —O—C(=O)CH$_2$—O—$R_5$, wherein $R_5$ is H, substituted or unsubstituted alkyl, alkenyl, cycloalkyl, aryl, or arylalkyl, wherein $R_1$, $R_2$, $R_3$ and $R_4$ are independently the same or different and are substituted or unsubstituted alkyl, alkenyl, cycloalkyl, aryl, or arylalkyl.

This invention also provids a composition comprising (a) a compound having the structure:

wherein X is O, or S and Y is —O—C(=O)CH$_2$—O—$R_5$, wherein $R_5$ is H, substituted or unsubstituted alkyl, alkenyl, cycloalkyl, aryl, or arylalkyl, wherein $R_1$, $R_2$, $R_3$ and $R_4$ are independently the same or different and are substituted or unsubstituted alkyl, alkenyl, cycloalkyl, aryl, or arylalkyl and (b) an organic solvent.

In one embodiment of the composition, the compound is at a concentration of 0.05 to 2.0 molar.

In another embodiment of the composition, the compound is at a concentration of 0.1 to 1.5 molar.

In another embodiment of the composition, the compound is at a concentration of 0.2 to 1.0 molar.

In a further embodiment of the composition, the compound is at a concentration of 0.4 to 0.8 molar.

For the purposes of this invention the term ferroelectric switching refers to the switching of light transmission when an electric field is applied. The term liquid crystal refers to liquid crystals comprising helicene molecules where the aromatic core are twisted helically and having the capacity to undergo ferroelectric switching.

In the present invention alkyl includes, but not limited to compounds having the structure $C_nH_m$ wherein n is an integer ≧3 and m is an integer −2n+1.

For the purposes of this invention, the alkenyl includes, but not limited to compounds having the structure $C_nH_m$ wherein n is an integer ≧3 and m is an integer ≦2n+1.

For the purposes of this invention, the cycloalkyl includes, but not limited to $C_3$–$C_{30}$ cycloalkyls.

For the purposes of this invention, the aryl includes, but not limited to phenyl and naphthyl.

For the purposes of this invention, the arylalkyl includes, but not limited to phenyl substituted with alkyl having the structure $C_nH_m$ wherein n is an integer $\geq 3$ and m is an integer $\leq 2n+1$.

This invention will be better understood from the Experimental Details which follow. However, one skilled in the art will readily appreciate that the specific methods and results discussed are merely illustrative of the invention as described more fully in the claims which follow thereafter.

Experimental Details

Columnar liquid crystals that are titled and have dipole moments perpendicular to the column axes exhibit ferroelectric properties.[1] Although such properties might also be shown by columnar mesophases that have large dipole moments parallel to the column axes,[56] only few such structures are available to test.[16,57-66] Nonracemic helicene 1 is one.[22] It forms a columnar mesophase, and the columns are packed on an hexagonal lattice,[22] which ideally should mean they are ordered parallel to one another.[57-63, 67,68] Moreover, in the absence of an electric field, the columns align themselves with their stacking axes parallel to a rubbed glass surface, giving rise to the planar texture. Therefor an electric field perpendicular to the surface should redirect them[69-70] as it does other disc-shaped molecules.[71-72] The texture should become homeotropic. Thus columns that are parallel to the surface, and therefore anisotropic in the surface's plane, should reorient so as to be isotropic in this plane. The former orientation would be birefringent, the latter not. Only in the former could light be transmited if the sample were sandwiched between crossed polarizers. The experiments described below show that such switching can be achieved. The rate of switching and its dependence on both temperature and the strength of the electric field that induces the switching are analyzed.

General Methods for Preparing the Liquid Crystals

Scheme 1 shows how nonracemic compound (+)-2b was synthesized, by using sodium dithionite to reduce both quinone functions of enantiomerically pure compound 1 to hydroquinones.

Tetrahydrofuran (THF) was distilled from Na plus benzophenone, $CH_2Cl_2$ and $Et_3N$ from $CaH_2$. Benxyloxacetyl chloride (95%) was purchased from Aldrich Chemical Company and used without further purification.

Compound (+)-2b in THF (3 mL) was added to compound (+)-1(30 mg, $2.7\times10^{-5}$ mol) and $Na_2S_2O_4$ (60 mg $3.45\times10^{-4}$ Mol) under $N_2$, followed by deoxygenated water (1.5 mL). The mixture was stirred until the deep wine-red color had changed to a brilliant lemon-yellow color (approximately 10 minutes) $CH_2Cl_2$ (3 mL) was injected and the lower organic layer, followed by two further $CH_2Cl_2$ extracts, was transferred to another dry bottomed flask.

After concentration under induced pressure and drying for 12 hours in a vacuum, THF (3 mL) containing compound (+)-1 (30 mg, $2.7\times10^{-5}$ mol) was added under $N_2$ and after the mixture had stirred for 5 minutes at room temperature and been cooled to 0° C., α-benzyloxyacetyl chloride (42 μL. $2.7\times10^{-4}$ mol) was injected, followed by $Et_5N$ (200 μL 1.43× $10^{-3}$ mol) added in drops. The reaction mixture was stirred at room temperature for 3 hours, and after saturated aqueous $NaHCO_3$ (ca. 2 mL) has been added, it was stirred for 1 hour. After extraction with benzene (3 times), washing with 1 N aqueous HCl, water and saturated aqueous $NaHCO_3$, drying ($MgSO_4$) filtering and removal of solvent, the crude produce was chromatographed 3 times on a 1 inch by 6 inch silica gel column eluting with 2% EtOAc/benzene. The yield of compound (+)-2b, an orange oily wax, was 55 mg (72%). IR (KBr)2923, 2853, 1772, 1662, 1599, 1516, 1498, 1467, 1375 cm$^{-1}$; $^1$H NMR (1400 MHZ. $CDCl_3$) δ0.88 (t, 12H, J=6.5 Hz). 1.20–1.50 (m, 72 H), 1.53–1.65 (m, 8 H), 1.92–2.05 (m, 8 H), 2.93 (d, 1 H. J=16.8 Hz), 3.41 (d, 1 H. J=16.8 Hz), 4.18 (s, 2 H), 4.10–4.40 (m, 8 H), 4.56 (s, 2 H), 4.84 (d, 2 H, J=1.8 Hz.) 6.22 (d, 1 H, J=10.2 Hz), 6.41 (d, 1 H, J=10.2 Hz), 6.70 (d, 1 H, J=8.4 Hz), 7.01 (s, 1 H), 7.09 (d, 1 H, J=8.4 Hz), 7.17–7.19 (m, 2 H), 7.26–7.48 (m, 9 H), 7.54 (s, 1 H), 7.74 (s, 1 H). $^{13}$C NMR (75 MHz, $CDCl_3$) δ14.11, 22.69, 26.20, 26.39, 26.47, 29.06, 29.12, 29.38–29.75 (m), 31.92, 66.31, 67.24, 68.43, 69.22, 69.33, 69.56, 73.06, 73.66, 99.6, 97.7, 101.6, 101.8, 116.8, 118.2, 119.5, 121.1, 121.6, 124.9, 127.4, 127.7, 127.9, 128.1, 128.2, 128.3, 128.5, 128.6, 130.0, 130.3, 134.5, 136.8, 136.9, 139.8, 143.0, 143.3, 153.3, 156.4, 156.5, 158.0, 167.5, 169.2, 185.2, 185.7. (HRMS) (M+1) calculated for $C_{92}H_{127}O_{12}$ 1423.9328, found 1423.9349.

Concentration Effects on CD, UV-vis Absorption, Florescence Emission, and $^1$H NMR Spectra, Polarimetry UV-vis absorption spectra was recorded with a Perkins-Elmer Lambda 19 UV-vis spectrometer, circular dichroism spectra with a JASCO 720 spectrometer, florescence spectra with a Spex Flouring 56 flourament, and optical rotations with a JASCO Dip 1000 polarimeter. The solvent used was olefin-free dodecane from Fluka. To measure the spectra of $2.1 \times 10^{-2}$ M solution at a 10 µm quartz cell from Starna Cells was used and for the $2.1 \times 10^{-5}$ M solution a 1 cm quartz cell. The florescence spectra was measured by the front face emission from the 1 µm quartz cell. The neat samples were prepared by spin coating from a $1 \times 10^{-3}$ M hexane solution at 6000 rpm. A plate holder allowed the samples to be rotated through 360° at 30° increments. $^1$H NMR spectra of $2 \times 10^{-2}$ and $2 \times 10^{-4}$ M solution is deuterated dodecane (Cambridge Isotope Labs) at 50° C. were acquired on a 500 MHZ. Bruker NMR spectrometer, and the chemical shifts were referenced to internal TMS.

X-Ray Diffraction, DSC, and Polarized Microcopy:

A Leica DMRXP polarizing microscope and an attached Wild Leitz MPS46 camera were used to view and photograph samples sandwiched between a microscope slide and coverslip. The samples were heated in a Mettler FP 80HT central processor. We prepared the rubbed glass samples using a coverslip and microscope slide both of which had been rubbed multiple times in the same direction, first with a lint-free wiper and then with a lint-free wiper wetted with a drop of ethanol.

The sample for X-Ray diffraction was warmed, made to flow into a 1.5 mm Linderman capillary tube and thermostated in a heating block whose temperature was controlled to ±1° C. by a Minco CT 137 controller. Ni-filtered Cu Ka radiation from a fine-focus X-ray tube and XRG 2000 generator and an Intel CPS 120 position-sensitive detector, calibrated with a mica standard from the National Bureau of Standards, were used to record the X-ray diffractogram.

A Perkins-Elmer DSC 7 equipped with a Perkins-Elmer 7700 is used for the differential scanning calorimetry measurements.

Polarized Light Microscopy

Compound (+)-2b is a yellow-orange viscous liquid that is birefringent at room temperature. As it is heated it becomes a mobile liquid, which becomes isotropic at 85° C. No crystalline phase was seen. The texture displayed in FIG. 1 forms when an isotropic liquid sample on a unidirectionally rubbed glass plate[28] is cooled to 84.6° C. and held at this temperature for 30 minutes. The features seen in the figure are ca. 13 µm by 5 µm in size, uniaxial, and negatively birefringent. However, the sample's absorption of visible light obscured details,[29] and we failed to identify the texture. Although it may be unique, it resembles that in a published photograph of a chiral cyclotriveratrylene.[16]

Differential Scanning Calorimetry

Heated in the calorimeter at a rate of 2° C./min, compound (+)-2b undergoes a broad endothermic transition (16.14 kJ/mol) beginning at 74.3° C. and maximizing at 83.6° C. No other phase transition was detected up to 150° C. On cooling, the sample undergoes an exothermic transition (−19.30 kJ/mol) beginning at 74.0° C. and maximizing at 71.8° C. The absence of other transitions and the similarity of the enthalpies measured to the ca. 1–20 kJ/mol associated with transitions from columnar discotic mesophases to isotropic liquids[30-33] supports the hypothesis that compound (+)-2b is liquid crystalline from room temperature to its clearing point.

CD Spectra, UV-Vis Absorption Spectra, and Specific Rotations

Figure 2:
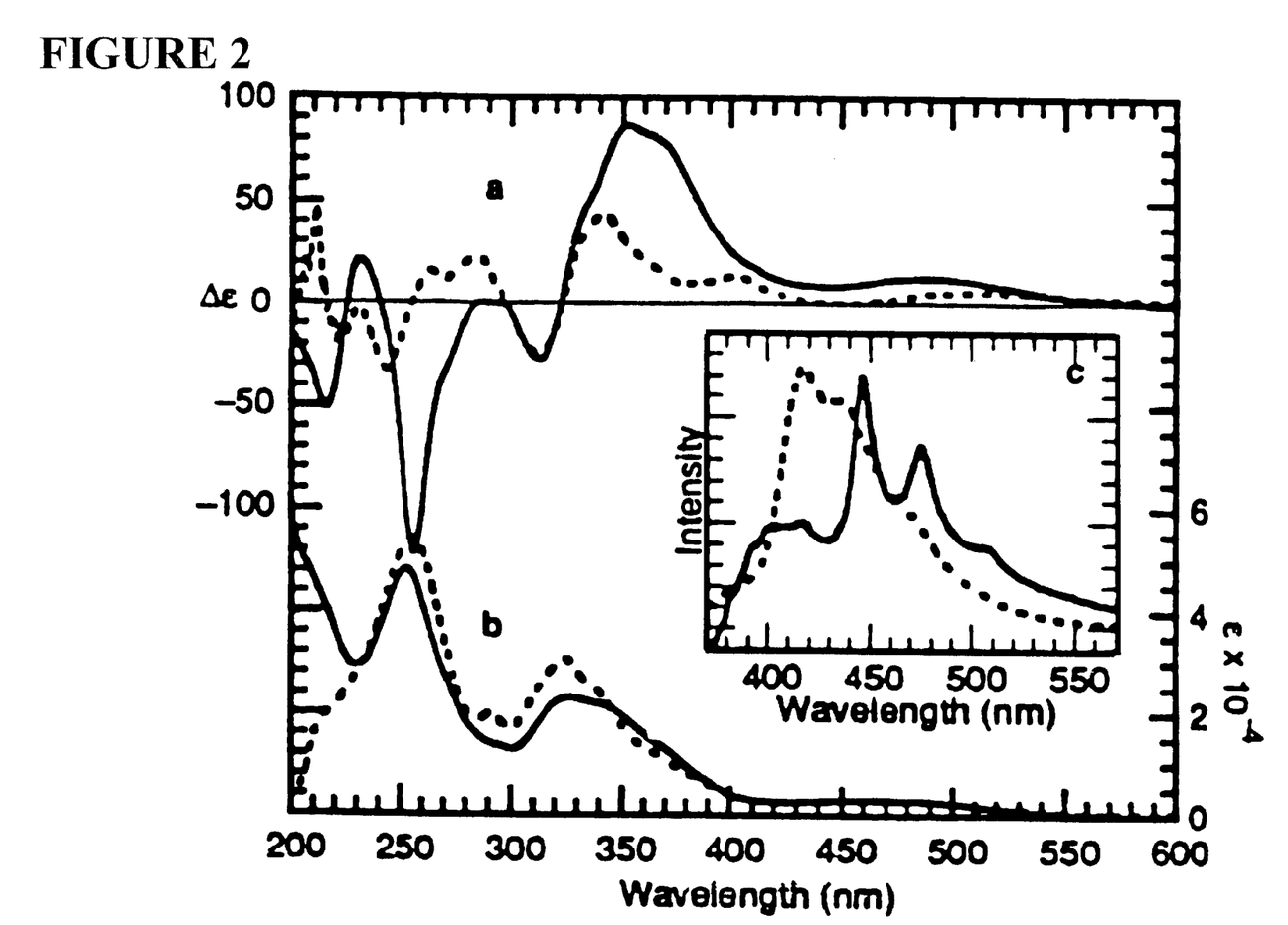
FIG. 2. (a) CD spectra (ordinate on the left, displaying molar circular dichroism) and (b)UV-vis absorption spectra (ordinate on the right, displaying molar extinction coefficients) of compound (+)-2b in n-dodecane: "-" represents data when the concentration is 2.0×10$^{-2}$ M and the path length is 10 μm and "---" represents data when the concentration is 2.0×10$^{-5}$ M and the path length is 1 cm. The inset (c) displays the emission spectra (excitation at 320 nm) of the same solutions. Both in 10 μm cells.

When solutions of compound (+)-2b in dodecane are concentrated, their CD spectra, UV-vis absorption spectra, specific rotations, and viscosity all change, just as these properties change when solutions of nonracemic compound 1 in dodecane are concentrated. The implication is that the molecules of nonracemic compound (+)-2b, like those of nonracemic compound 12 and a number of other molecules,[34-36] aggregate in solution. Thus, when the concentration of a solution of compound (+)-2b in dodecane is increased from $2.0 \times 10^{-5}$M to $2.0 \times 10^{-2}$ M, the viscosity increases and the specific rotation rises from 773 deg·cm$^2$/10 g to 2810 deg·cm$^2$/10 g. Moreover, the changes that occur in the CD spectra, the UV-vis absorption spectra (FIGS. 2a and 2b), the fluorescence emission spectra (FIG. 2c), and the chemical shifts of the $^1$H NMR spectra are similar to those that occur when solutions of nonracemic compound 1 are concentrated.

An intense circular dichroism appears in the concentrated solution at 256 nm ($\Delta\epsilon = -120$), whereas there is no appreciable circular dichroism at this wavelength in the dilute solution. (In the spectra of nonracemic compound 1, the new CD peak that appears on concentration is at 251 nm.) In the spectrum of the concentrated solution of compound (+)-2b, a broad and intense CD appears at 352 nm, while in the spectra of nonracemic compound 1, the similar peak is at 343 nm. The UV-vis absorption spectrum of compound (+)-2b changes much less than the CD spectrum when the solutions are concentrated (FIG. 2), which is true also for the solutions of compound 1.[21] However, the fluorescence emission spectrum shifts considerably (30 nm in FIG. 2c), as does that of nonracemic compound 1, and the shifts in both cases-to the red on concentration-are in the same direction as when hexapentyloxytriphenylene assembles into columnar discotic mesophases[37] and when its solutions in cyclohexane are concentrated.[28] The implications are that nonracemic compound (+)-2b, like nonracemic compound 1 [21,22] and like hexapentyloxytriphenylene, aggregates when its solutions in dodecane are concentrated and that the structure of the aggregates is columnar.

The changes that occur in the $^1$H NMRs when a solution in deuterated dodecane is concentrated accord with such a structure. All seven of the eight aromatic proton resonances that were observed shifted to higher fields by between 0.04 and 0.13 ppm, similar to the shifts seen when solutions of compound 1 are concentrated.

Thin Films

Figure 3:
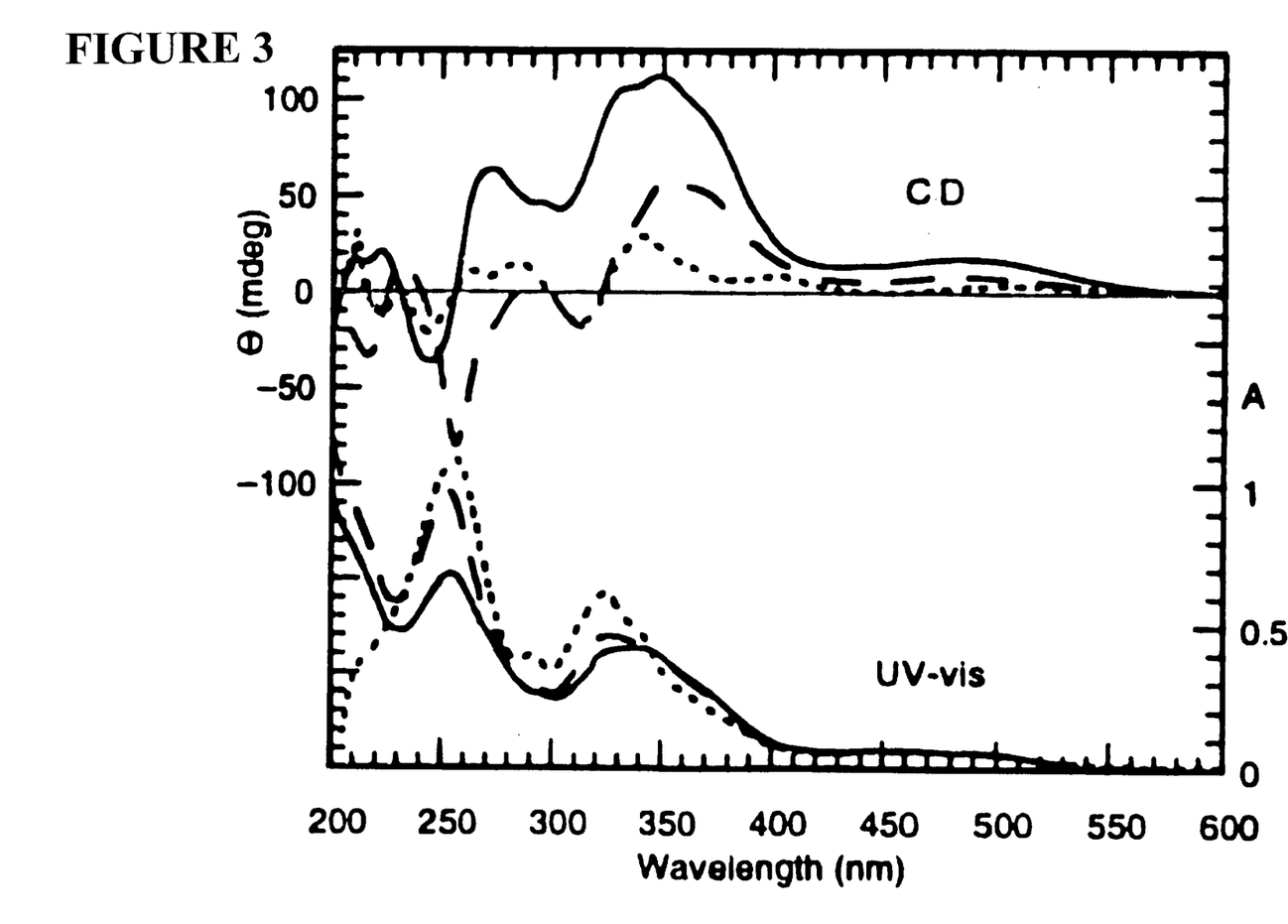
FIG. 3. CD and UV-vis spectra(-) of a thin film. "--" represents spectra of a 2.0×10$^{-2}$ M solution of dodecane (path length 10 m), and ". . ." represents spectra of a 2.0×10$^{-5}$ M solution in dodecane(path length 1 cm). The UV-vis and CD spectra of the film were multiplied by 1.18 to make the film's UV-vis absorbance at 344 nm equal those of the solutions.

Films were produced by spin-coating compound (+)-2b from a $1 \times 10^{-3}$ M hexane solution onto quartz plates. Shown in FIG. 3 are the CD and UV-vis absorption spectra of one of these films. The CD spectra did not change appreciably when the sample was rotated in a plane perpendicular to the light beam, but to eliminate any effects due to linear dichroism or linear birefringence, the CD spectrum displayed is the average of the spectra determined as the sample was rotated through six 30° increments.[40-44] Both the CD and UV-vis absorption spectra of the films differ from the spectra of a $2.0 \times 10^{-5}$ M solution in dodecane (also in FIG. 3), at which concentration the molecules are presumably isolated from one another. The films rotate plane polarized light at the D-wavelength (589 nm) by 0.018±0.004° (this value too is the average of six measured as the sample was rotated through 30° increments). If the assumption is made that the extinction coefficient of the film at 344 nm is the same as that of the two solutions in dodecane, $[\alpha]_D$ can be estimated to be 9,600 deg·cm$^2$/10 g measured for the $2.0 \times 10^{-5}$ M dodecane solution.

The most noteworthy observation drawn from FIG. 3, which compares the CD and UV-vis absorption spectra of compound (+)-2b as a $2.0 \times 10^{-5}$ M solution in dodecane, as a $2.0 \times 10^{-2}$ M solution in dodecane, and as a thin film of the pure material, is that as the concentration increases, the CDs increase and the absorption intensities decrease. That is, the g-values ($\Delta\epsilon/\epsilon$) rise greatly, which agrees with the hypothesis that assembly into columns increases with concentration.[21] For the $2.0\times10^{-5}$ M solution, the g-value at 244 nm is $5.8\times10^{-4}$; for the film, it is $2.8\times10^{-3}$. The corresponding values for the peaks at 350 nm are $1.8\times10^{-3}$ for the dilute solution and $9.1\times10^{-3}$ for the film.

Ray Diffraction

Figure 4:
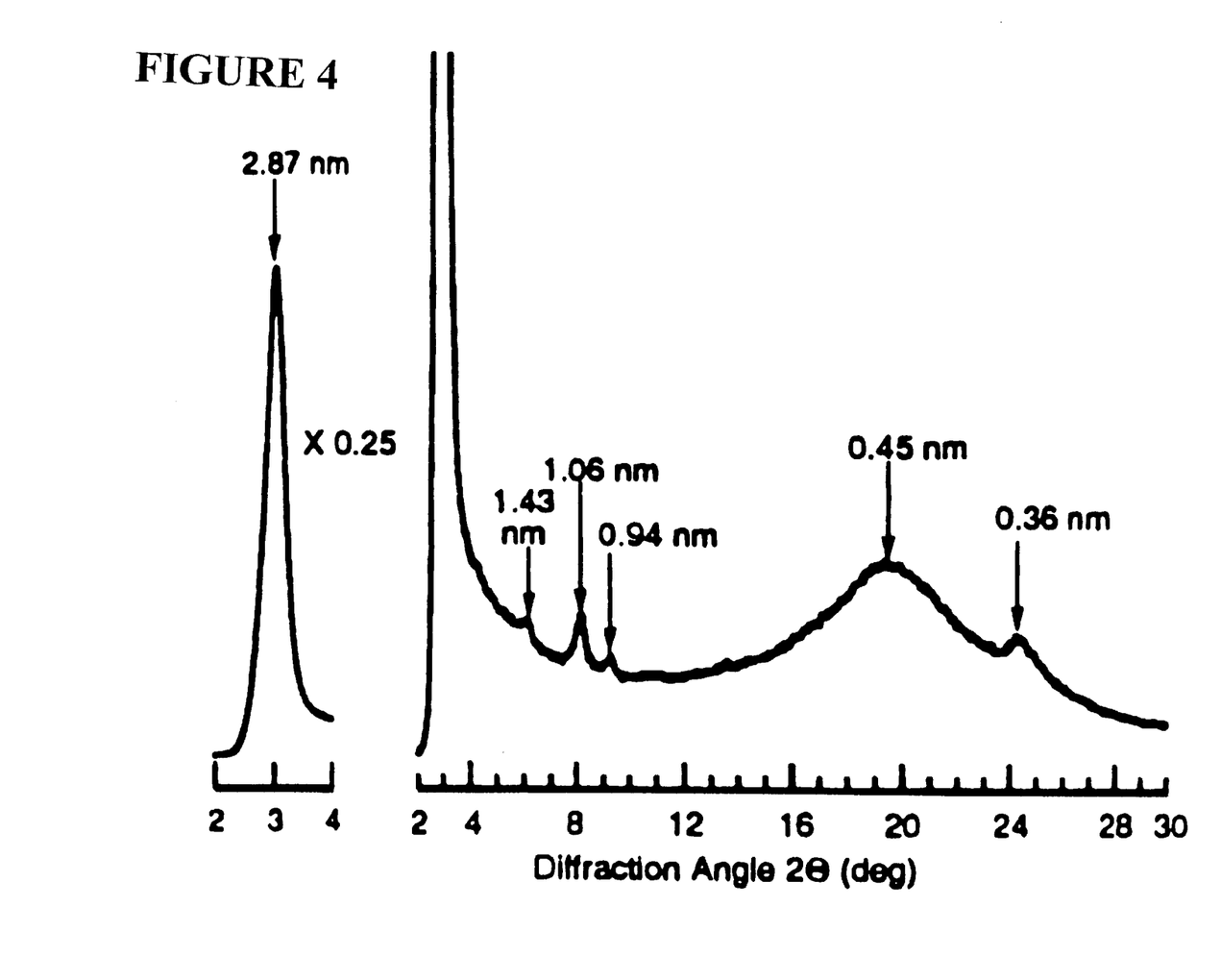
FIG. 4. Diffraction pattern from a capillary tube filled with compound (+)-2b at 75° C.
Figure 5:
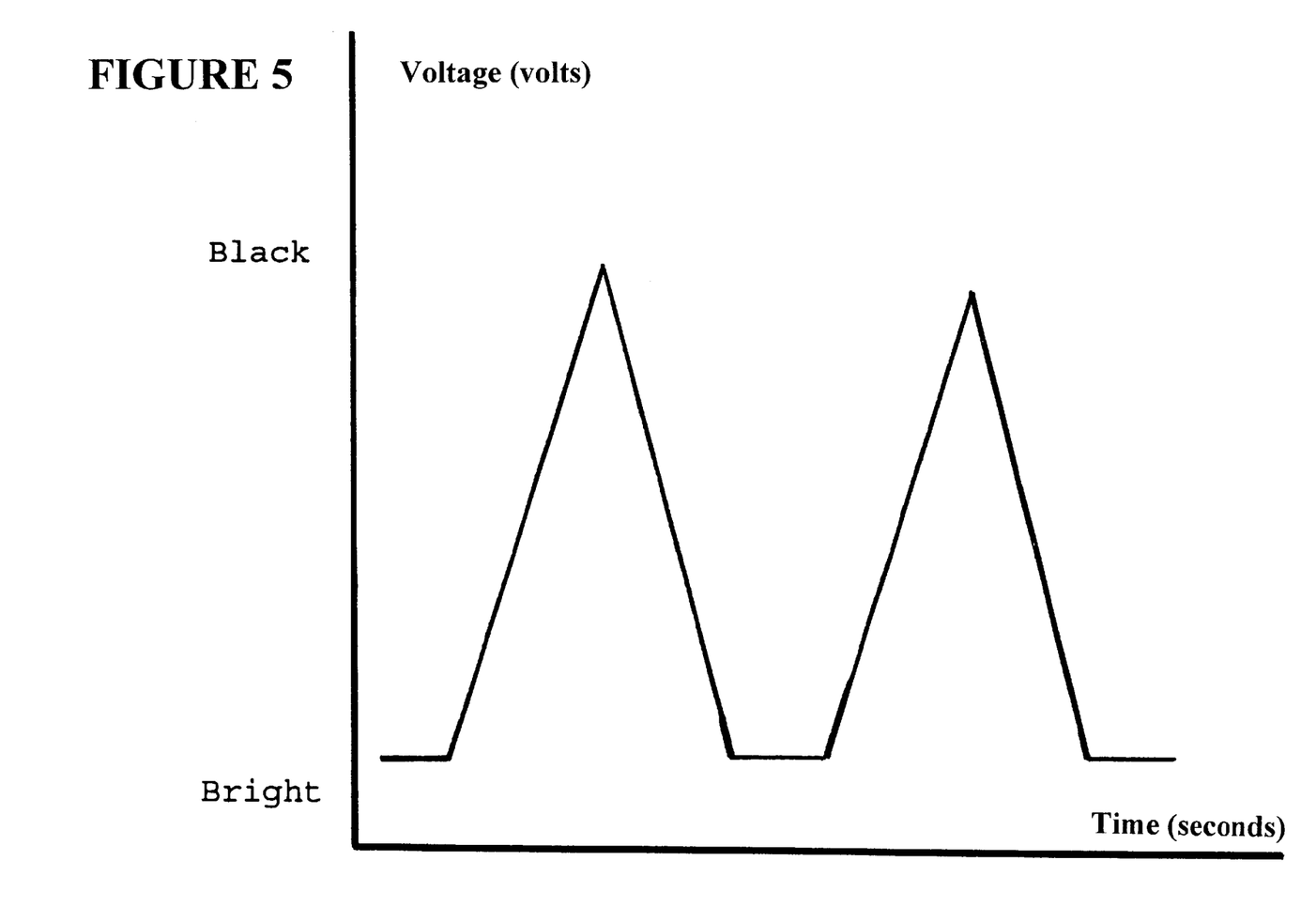
FIG. 5. Switching of light. A triangular electric wave having a peak to peak voltage of at least 20 volts was applied to liquid crystal of compound (+)-2b deposited on rubbed glass to generate light switching effect; wherein "bright" indicates that the liquid crystal transmits light and "black" indicates that the liquid crystal does not transmit light.
Figure 6:
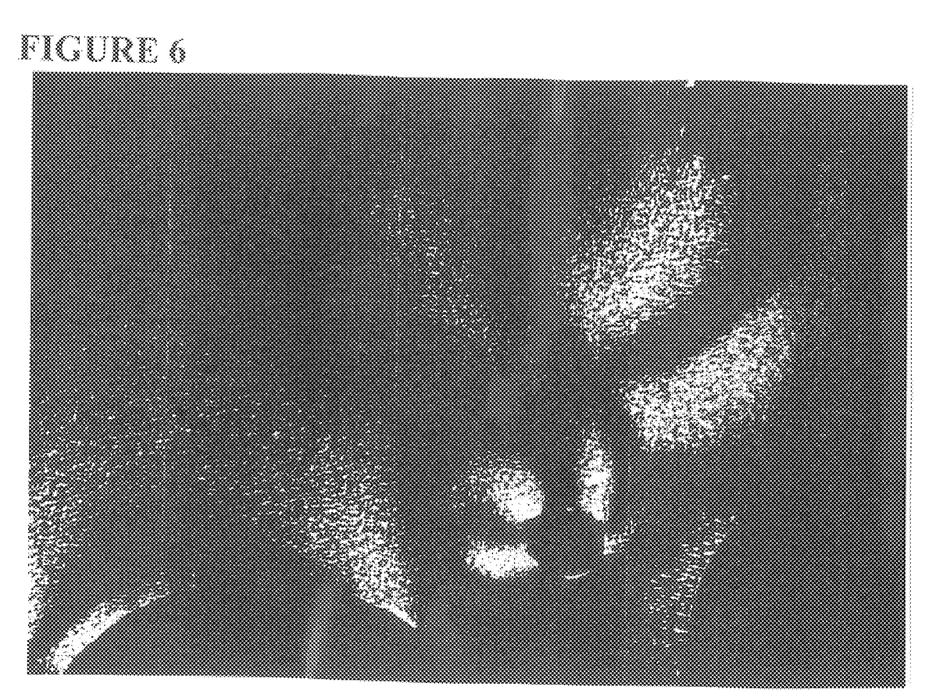
FIG. 6. Microscopic view of pure compound (+)-2b that had been cooled from the clearing temperature to 80° C. in a 4 μm nylon-lined cell. The sample is between crossed polarizers.

FIG. 4 shows the diffraction pattern of compound (+)-2b that had been warmed in a capillary tube to 100° C. and then cooled to 75° C. The diffractogram is essentially the same if the material is cooled further to room temperature. The peaks at low angles can be indexed as reflections from a hexagonal lattice: 2.87 nm (100), 1.43 nm(200), 1.06 nm (210), and 0.94 nm (300). These peaks, as well as the broad one at 0.45 nm, are characteristic of the diffractograms of compound 1 and of columnar discotic liquid crystals, the former set representing reflections from planes of columns and the latter the distance between the alkyl side-chains.[23] The reflection at 0.36 nm is also observed in the diffractions from many ordered columnar discotic liquid crystals and has been attributed to their n-n stacking distance.[29,31,47-55]

There are two notable differences between the X-ray diffractograms of compound (+)-2b and of compound 1. One is that the 0.36 nm reflection, observed for compound (+)-2b, is not seen in the diffractogram of compound 1,[17-19] which suggests that the order along the lengths of the columns is greater in the former than in compound 1.[29,47-55] The other is that the column diameter is smaller in compound (+)-2b (3.3 nm) than in compound 1 (4.1 nm), which while it might be attributed to greater interpenetration or folding of the side-chains in compound (+)-2b, might more plausibly be a consequence of the rings being tilted. This could be a consequence of steric crowding by the substituent on the interior of the ring system or of the molecules of compound (+)-2b having a dipole moment that is not parallel to the helix axis, the rings tilting to minimize the intermolecular dipolar interaction energy. The greater order along the lengths of the columns in compound (+)-2b, compared to compound 1, might also be a consequence of greater dipole-dipole (or donor-acceptor) interactions. How the structural difference account for the lower clearing temperature of compound (+)-2b than that of compound 1 is, however, unclear.

Preparation of Other Liquid Crystals

Based on the new principle of switching light and the characteristics of compound (+)-2b, a person of ordinary skill in the art could derive other compounds from compound (+)-2b which also form liquid crystals having a dipole moment from one end of the molecule to the other, having a chiral core, and being disk-shaped. In addition, compound (+)-2b also aggregates in solution and the optical properties in both the pure material and the aggregates in solution are enhanced in comparison to the isolated molecules.

Without relying on or to be bound by a particular theory, it appears that the —$C_{12}H_{25}$ of compound (+)-2b may be substituted by any nonpolar groups such as an alkyl, an alkenyl, a cycloalkyl, an aryl or an arylalkyl while maintaining the dipole moment, the chiral core and the light switching properties of compound (+)-2b. The —Bn residue on $R_5$ of compound (+)-2b may be substituted with other chemical groups such as a hydrogen, an alkyl, an alkenyl, a cycloalkyl, an aryl, or an arylalkyl and such derivatives of compound (+)-2b will also have the dipole moment, the chiral core and the light switching properties similar to those of compound (+)-2b.

Liquid crystal of a compound wherein $R_5$ is —$C_6H_5$ according to Scheme 1 except that $C_6H_5CH_2OCH_2COCl$ is substituted by $C_6H_5OCH_2COCl$.

Liquid crystal of a compound wherein $R_5$ is —$C_6H_{11}$ according to Scheme 1 except that $C_6H_5CH_2OCH_2COCl$ is substituted by $C_6H_{11}OCH_2COCl$.

Liquid crystal of a compound wherein $R_5$ is —$CH_2CH_2CH_2CH_2CH_2CH_3$ according to Scheme 1 except that $C_6H_5CH_2OCH_2COCl$ is substituted by $CH_3CH_2CH_2CH_2CH_2CH_2OCH_2COCl$.

Liquid crystal of a compound wherein $R_5$ is —$CH_2CH_2CH_2CH=CHCH_3$ according to Scheme 1 except that $C_6H_5CH_2OCH_2COCl$ is substituted by $CH_3CH=CHCH_2CH_2OCH_2COCl$.

Liquid crystal of a compound wherein $R_5$ is —$CH_{10}H_9$ according to Scheme 1 except that $C_6H_5CH_2OCH_2COCl$ is substituted by $C_{10}H_9OCH_2COCl$.

General Methods for Making and Testing Liquid Crystal Samples with Light and Conductivity Switching Properties Disclosed is a new way to switch the transmission of light and electric current by applying an electric field. Such switches are the essential features of display devices such as those in calculators, digital watches, flat panel computer screens and flat panel televisions. This invention uses a new principle to effect the switching. One example of the materials for switching is a nonracemic helicene that is surrounded by alkyl chains and that has a dipole moment directed from one end of the helicene to the other. When sheared or deposited onto a rubbed substrate, the molecules organized in columns with helix axes parallel to the surface (so-called planar orientation) and the material was consequently birefringent. When a voltage was applied perpendicular to the surface, the molecules reoriented so the helix axes are perpendicular to the surface (the homeotropic orientation). In this orientation, the material was not birefringent, and therefore, no light was transmitted when it was between crossed polarizers. When the electric field is turned off, the orientation of the molecules changes from homeotropic to planar and light is transmitted again.

The switching of light can be induced by either an electric square wave or an triangular wave. However, an electric triangular wave is preferred for better switching results. The light switching effect of the sample can be observed at a peak to peak voltage of the electric wave between 20 and 2,000 volts, preferably between 60 and 1,000 volts.

The switching of conductivity can be observed by applying an electric wave having a peak to peak voltage between 250 and 2000 volts, preferably between 300 and 1,000 volts.

Helicene compound (+)-2b forms the first disk-shaped liquid crystal having a dipole moment from one end of the molecule to the other, having a chiral core, and being disk-shaped.

EXAMPLE 1

Figure 1:
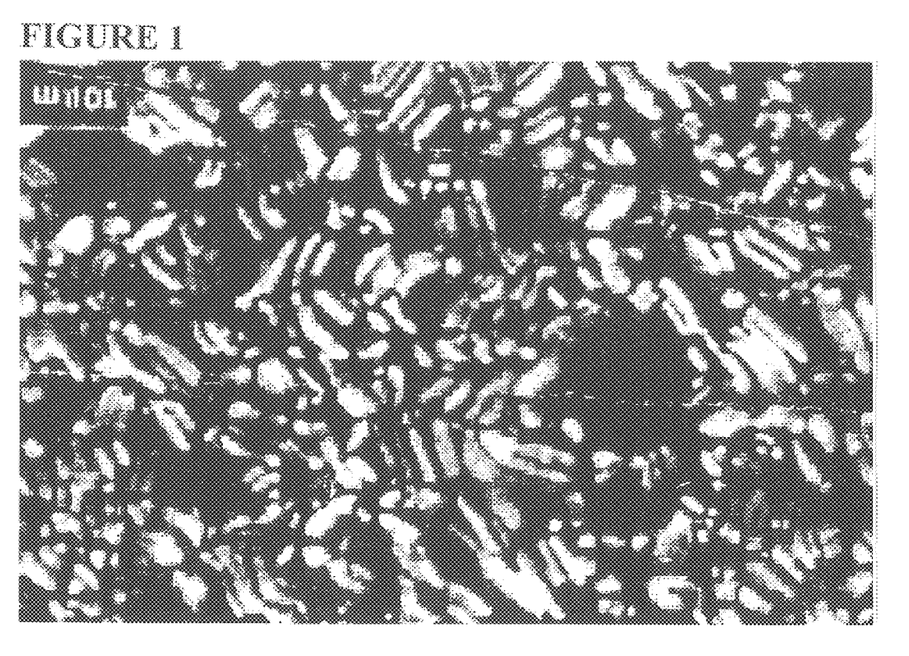
FIG. 1. Optical micrograph of compound (+)-2b of Scheme 1 from the isotropic liquid to 84.6° C. between crossed polarizers.

Compound (+)-2b was first examined pure in a 4 $\mu$m nylon-lined cell, into which it was allowed to flow as an isotropic liquid at ca. 100° C. The sample in the cell was heated again until it was isotropic (more than 85° C.) and then cooled to 80° C. FIG. 1 shows a microscopic view at this temperature between crossed polarizers. The material is birefringed and exhibits small and irregular patters as well as a texture similar to that of nematic liquid crystals. If the sample is subjected to a steady electric field produced by the application of 60 V or more (but not less), light ceases to be transmitted. The sample is no longer birefringent. As the field-strength required is high and the switching time is long, the experiments were repeated with samples that were diluted with solvent.

EXAMPLE 2

As the mesophase formed by (+)-2b, like that of other columnar materials,[73] is too viscous to reorient quickly in an approppriate electric field, the possibility was considered that diluting the sample with solvent would produce a lyotropic mesophase that would be less viscous, but would still be columnar and in an electric field would still reorient its direction.[23,39,74-80]

Dodecane as the solvent chosen because at concentration of 4 wt % and possibly less compound (+)-2b is organized in it into aggregates that, like those of a related helicenebisquinone,[23,78-79] are probably columnar.[22] In the presence of an electric field, compound (+)-2b, 17 wt % solutions, was warmed and loaded into cells of the same size as before. Also as before, compound (+)-2b in the cell was heated to ca. 100° C., at which temperature and between crossed polarizerd, it appeared isotropic.

Figure 7:
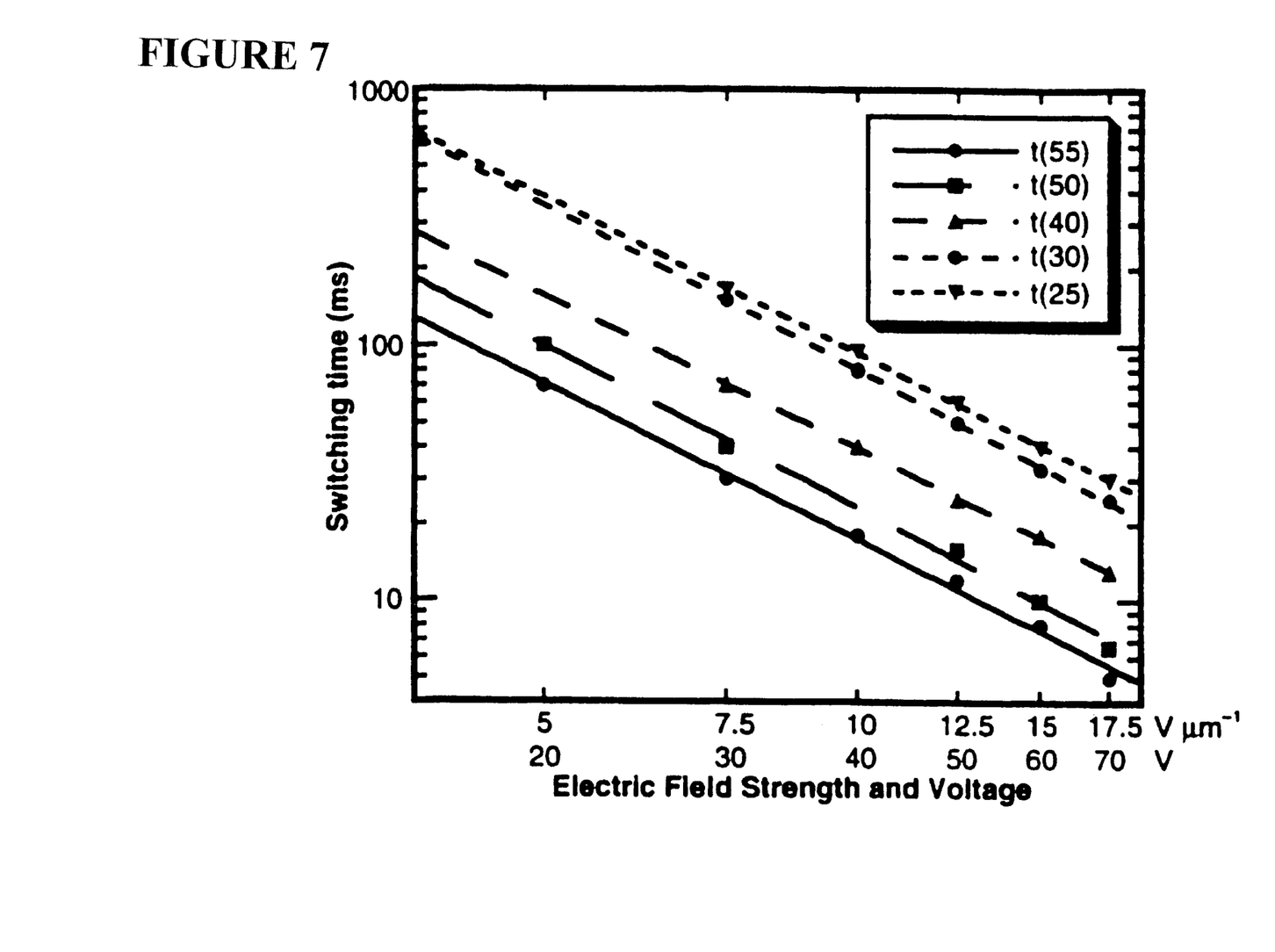
FIG. 7. Microscopic view of a 17 wt % solution of compound (+)-2b in dodecane in a 4 μm nylon-lined cell and in an electric field of 3.1 V $\mu m^{-1}$. The sample is between crossed polarizers. The area covered by the electrodes (which are transparent) is black; the other areas are bright.
Figure 8:
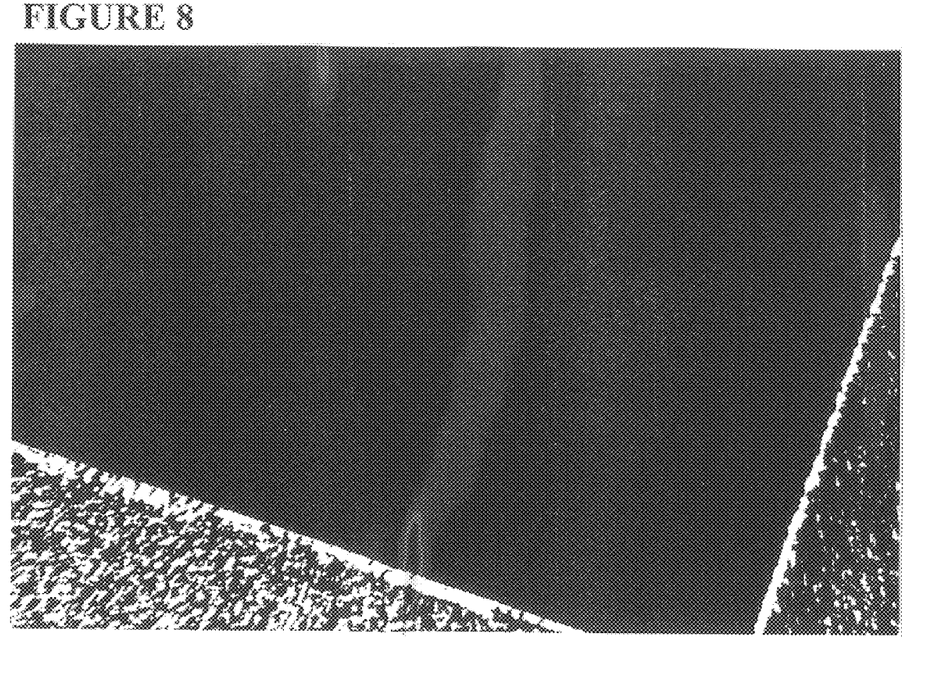
FIG. 8. At five temperatures and as a function of voltage, the switching times for the extinction of light transmittance by the sample pictures in FIG. 7. The scales for both the abscissa and the ordinate are logarithmic.

However, when cooled to 50° C., the sample was birefrigent. Sandwiched between crossed polarizers, it transmitted light fairly uniformly across the area of the electrodes, and when it was rotated (by approximately 35° between the two pictures) in the plane of the polarizers, the transmitted light could almost be extinguished. The implication is that the sample has a uniform uniaxial orientation. If the light-transmitting sample between crossed polarizers was subjected to an electric field directed in either way perpendicular to the polarizers, the light was totally extinguished. FIG. 7 shows this. The material covers the whole area of FIG. 7, but the area is black where, and only where, it is between the electrodes.

There is a threshhold of 2.45 V $\mu m^{-1}$ at which the switching to opacity occurs. When the eletric field was turned off, the transmission of light was restored. The implications are that the molecules are organized in columns, that these columns are parallel to one another, and that in the absence of an electric field the columns lie parallel to the surfaces, in the planar texture. In an electric field of 2.45 V $\mu m^{-1}$ or more they reorient so as to be perpendicular to the surfaces, in the homeotropic texture. When a low voltage was applied, a rippling could be observed, which means that the columns are so long they have to break to align themselves parallel to the 4 $\mu m$ short dimension of the cell.

EXAMPLE 3

The times for the material to become opaque (the switching times) were measured as a function of the strength of an applied eletric field produced by a 1 Hz square wave potential that varied from zero to a set maximum voltage. The measurements were made at five temperatures, and the data are displayed in FIG. 3. They show that at 55° C., the switching time in a field of −10 V $\mu m^{-1}$ (40 V) is 18 ms. At higher field stengths, it is less, for example at 17.5 V $\mu m^{-1}$, 5 ms. However, since ferroelectric materials switch at a rate proportional to the field strength,[81] while FIG. 3 shows that rates for the material studies here vary as the square of the field strength (the measured exponent is 2.06±0.05) the material bahaves as a dielectric, not a ferroelectric. The switching times at five voltages studied vary with temperature in accord with the Arrhenius equation. The activation energy is 11.90±0.7 kcal/mol (49.8±3 kJ/mol, or 8.27±0.5× $10^{-20}$ J/molecule).

EXAMPLE 4

1.8 mg of helicene compound (+)-2b, was added into a DSC pan and then dodecane was added into the same DSC pan to solubilize the helicene compound (+)-2b. The helicene compound (+)-2b sample, i.e. the dodecane solution of the helicene compound (+)-2b, was heated at 100–120° C. until the total weight was between 3.6 mg and 7.2 mg. The helicene compound (+)-2b sample contains between 1 and 3 parts of dodecane for each part helicene compound (+)-2b by weight. The helicene compound (+)-2b sample was then transferred quickly into a 4 $\mu l$ EHC cell with polyimide coating that had been rubbed and heated until 100° C. The helicene compound (+)-2b sample was placed under microscope with cross polarizers. The helicene compound (+)-2b sample in EHC cell appeared birefringed and the birefringed sample could be extinguished by rotating the stage.

EXAMPLE 5

1.8 mg of helicene compound (+)-2a, is also added into a DSC pan and then dodecane is added into the same DSC pan to solubilize the helicene compound (+)-2a. The helicene compound (+)-2a sample, i.e. the dodecane solution of the helicene compound (+)-2a, is heated at 100–120° C. until the total weight is between 3.6 mg and 7.2 mg. The helicene compound (+)-2a sample contains between 1 and 3 parts of dodecane for each part helicene compound (+)-2a by weight. The helicene compound (+)-2a sample is then transferred quickly into a 4 $\mu l$ EHC cell with polyimide coating that has been rubbed and heated until 100° C. The helicene compound (+)-2a sample is placed under microscope with cross polarizers. The helicene compound (+)-2a sample in EHC cell appears birefringed and the birefringed sample can be extinguished by rotating the stage.

Furthermore, when a helical discotic switch is made using the new mesophase based on the new principle of switching light, it has a much greater effect on light transmission than other types of switches.

REFERENCE

1. Malhete, J., et al. (1982) Nature, 298:46–;
2. Bock, H. and Helfrich (1992) W. Liq. Cryst., 12:697–;
3. Bock, H. and Helfrich, W. (1995) Liq. Cryst.,18:387–;
4. Jakli, A, et al. (1998) Liq. Cryst., 24:467–;
5. Scerowsky, G. and Chen, X. H. (1995) J. Mater. Chem., 5:417–;
6. Langer, M., et al. (1995) J. Mater. Chem., 5:693–;
7. Cho. I. and Lim, Y. (1988) Bull. Korean. Chem. Soc., 9:98–;
8. van Nostrum, C. F., et al. (1995) Chem. Eur. J., 1:171;
9. Barbera, J., et al. (1998) J. Am. Chem. Soc., 120:2908–;
10. Green, M. M., et al. (1990) Angew. Chem., Int. Ed. Engl. 29:1478–;
11. Gontarelli, G., et al. (1996) Helv. Chim. Acta., 79:220 and references therein;
12. Livolani, F., et al. (1989) Nature, 339:724–;
13. Mukkamala, R., et al. (1998) J. AM. Chem. Soc., 118:9498—and references therein;
14. Jeffery, G. A. and Wingert, L. M. (1992) Liq. Cryst., 12:179–;
15. Kohne, B. and Praefcke, K. (1984) Angew. Chem. Soc. Int. Ed. Engl., 23:82–;
16. Malthete, J. and Collet, A. (1987) J. Am. Chem. Soc., 107:7544–;
17. Praefcke, K., et al. (1987) Liq. Cryst., 22:113–;
18. Boden, N., et al. (1997) J. Mater. Chem., 7:601–;
19. Yamamura, K., et al. (1998) J. Chem. Soc. Chem. Commun., pages 443–;
20. Heppke, G., et al. (1996) Ferroelectrics, 179:203–;
21. Nuckolls, C., et al. (1996) J. Am Chem. Soc., 118: 3767–;
22. Nuckolls, C., et al. (1998) A. J Am. Chwm. Soc., submitted for publication;

23. Lovinger, A. J., et al. (1998) J. Am. Chem. Soc., 120:264–;
24. Verbiest, T., et al. (1998) Science, submitted for publication;
25. Reference 7 and its Supporting Information give us the details of the original synthesis and the evidence for the enantiomeric purity. A manuscript in preparation provides an improved preparation;
26. Taibushi, I., et al. (1987) J. Org. Chem., 52:2502–;
27. Tabushi, I., et al. (1987) Tetrahedron Lett., 28:2269;
28. Pelzl, G. (1994) In Liquid Crystals: Topics in Physical Chemistry, Stegenmeyer, H. Ed.; Springer: New York, Vol 3, pp 79–80;
29. Similar complications affect other colored compounds, such as Phihalocyanines; Sauer, T. (1993) Macromolecules, 26:2057–;
30. For a hexasubstituted benzene the value is 22 kJ/mol, see Chandrasekhar, S., et al. (1979) J. Phys. Collq. (Orsay. Fr.), C3:120–;
31. For some metallomesogens the values are between 0.4 and 7.5 kJ/mol, see Serrete, A. G., et al. (1994) Chem. Mater., 6:2252;
32. For triphenylenes the values are between 0.7 and 18.8 kJ/mol, see Destrade, C., et al. (1979) J. Phys Collq. (Orsay. Fr.), C3:17–;
33. For a truxene the value is 2 kJ/mol, see Warnerdam, T. W., et al. (1988) J. Liq. Cryst., 3:1087–;
34. Matile, S., et al. (1996) Chem. Biol., 3:379–;
35. Huang, D., et al. (1996) Heterocycles, 12:723 and references therein;
36. Schnur, J. M., et al. (1994) Science, 264:945–;
37. Markovisti, D., et al. (1995) J. Phys. Chem., 99:1005;
38. Braisbart, O., et al. (1988) Mol. Cryst. Liq. Cryst., 159:233–;
39. Sheu, E. Y., et al. (1989) J. Phys. (Paris) 50:1279–;
40. Kubal, H.-G. and Schonhofer, A. (1994) In Circular Dichroism Principles and Applications; Nakanishi, K., et al. (1994) Eds.; VCH: New York, Chapter 4;
41. Schonhofer, A. and Kubull, H.- G. (1987) Chem. Phys., 15:159–;
42. Norden, B. (1972) Acta Chem. Scand., 26:1763–;
43. Tunis-Schneider, M. J. B. and Maestre, M. F. (1970) J. Mol. Biol., 52:521–;
44. Cornell, D. G. (1979) J. Colloid Interface. Sci., 70:167–;
45. Kuhn, W. (1930) Trans. Faraday. Soc., 26:293–;
46. Eliel, E. L., et al. (1994) Stereochemistry of Organic Compounds, Wiley, New York, Chapter 13;
47. Simon, J. and Bassoul, P. (1989) In *Phihalocyamines: Properties and Applications;* Lenzoff, C. C.; Lever, A. B. P.; Eds.; VCH: New York, 1989 2:6;
48. Levelut, A. M., et al. (1981) *J. Phys.* (Paris) 42:147–;
49. Levelu, A. M. (1979) *J. Phys.* (Paris), 40 L-81;
50. Mohr, B., et al. (1995) J. Chem Soc. Chem. Commun., pages 995–;
51. Kumar, S., et al. (1993) *J. Org. Chem.,* 58:3821–;
52. Simon, J., et al. (1986) New J. Chem., 10:295–;
53. Foucher, P., et al. (1984) *Mol. Cryst. Liq. Cryst.,* 108:219;
54. Levelut, A. M. (1983) J. Chim Phys., 80:149–;
55. Heiney, P. A., et al. (1989) J. Phys.(Paris) 50:461–;
56. Piechocki, C. et al. (1987) *J. Mol. Cryst.,* 149:115;
57. Zheng, H., et al. (1993) *Liq.Cryst.,* 14:1421;
58. Zheng, H. X., et al. (1995) Chem. Mater., 7:2067;
59. Serrette, A. G. et al. (1993) J. Am. Chem.Soc., 115:8879;
60. Serrette, A. G. et al. (1994) Angew. Chem., Int. Ed. Eng., 33:2342;
61. Xu, B. Et al. (1993) J. Am. Chem. Soc., 115:1159;
62. Zimmermann,H., et al. (1985) Naturforsch. A, 40a: 149;
63. Levelut, A. M. et al. (1986) J. Phys., 47:351;
64. Wang, L. Et al. (1990) J. Chem. Phys., 142:335;
65. Jákli, A.; Saupe, A.; Scherowsky, G.; Chenm, X. H. Liq. Cryt. 1997, 22, 309.
66. Cometti, G., et al. (1990) *J. Chem. Soc., Chem. Commun.,*163;
67. Trzaska, S. T. et al. (1999) *J. Am. Chem. Soc.,* 121:4518;
68. Biscarini F., et al. (1991) Mol. *Phys.,* 73:439;
69. Heppke, G., et al. (1991) *Mol. Cryst. Liq. Cryst. Lett.* Sect., 8:17;
70. Raghunathan, V. A., et al. (1987) Mol. Cryst. Liq. Cryst., 148:77;
71. Palmans, A. R. A., et al. (1978) *Adv. Mater.,* 10:873;
72. Usol'teva, N., et al. (1994) Liq. Cryst., 20:731;
73. One second at 90° C. and 8 V $\mu m^{-1}$ in reference 2; 0.1 ms to 100 s in reference 3; 15–50 ms in reference 5; several seconds at 100° C. in reference 9.
74. Palmans et al., reference 71, used dodecane as a solvent, and Usol'tseva et al. reference 72 uses pentadecane. Both achieved switching using disc-shaped mesogens, but the switching times were very long, possibly hours for Uso'tseva et al. For Palmans et al. at an unspecified temperature, the switching times were between ca. 20 s and ca. 350 s, depending on the field strength, which ranged from 4.1 to 10 V $\mu m^{-1}$, and between ca. 5–10 s to 350 s at 2.5 V $\mu m^{-1}$, depending on the temperature, which ranged from 20 to 80° C.
75. Gabriel, J.-C., et al. (1996) *Langmuir,* 12:1690;
76. Schutte, W. J. Et al. (1993) *J. Phys. Chem.,* 97:6069;
77. Usoltseva, N. et al. (1998) *Bull Russ. Acad. Sci., Physical Ser.,* 62:1325;
78. Nuckolls, C., et al. (1999) J. Am. Chem. Soc., 121:79;
79. Nuckolls, C., et al. (1998) J. Am. Chem. Soc., 120:8656;
80. Fox, J. M., et al. (1999) J. Am. Chem. Soc., 121:2453;
81. Skarp, K. & Anderson, G. (1986) *Ferroelectric Lett.,* 6:67.

What is claimed is:

1. A helical discotic switch comprising: (a) liquid crystal having a spiral coil structure and a dipole moment along its axis, comprising a helicene compound having the structure:

wherein X is O, or S and Y is —O—C(=O)CH$_2$—O—R$_5$, wherein R$_5$ is H, substituted or unsubstituted alkyl, alkenyl, cycloalkyl, aryl, or arylalkyl, wherein R$_1$, R$_2$, R$_3$ and R$_4$ are independently the same or different and are substituted or unsubstituted alkyl, alkenyl, cycloalkyl, aryl, or arylalkyl; wherein the liquid crystal has the capacity to undergo ferroelectric switching, (b) a rubbed substrate deposited with the liquid crystal having a planar orientation, and (c) electrodes for applying an electric field perpendicular to the rubbed substrate which changes the orientation of the liquid crystal, thus preventing the transmission of light.

2. The helical discotic switch of claim 1, wherein $R_1$, $R_2$, $R_3$ and $R_4$ are substituted or unsubstituted alkyl or aryl.

3. The helical discotic switch of claim 1, wherein $R_1$, $R_2$, $R_3$ and $R_4$ are substituted or unsubstituted aryl.

4. The helical discotic switch of claim 1, wherein $R_1$, $R_2$, $R_3$ and $R_4$ have the structure $C_nH_m$ wherein n is an integer $\geqq 3$ and m is an integer $\leqq 2n+1$.

5. The helical discotic switch of claim 4, wherein $R_1$, $R_2$, $R_3$ and $R_4$ have the structure $C_nH_m$ wherein n is an integer from 3 to 50 and m is an integer from 7 to 101.

6. The helical discotic switch of claim 4, wherein $R_1$, $R_2$, $R_3$ and $R_4$ have the structure $C_nH_m$ wherein n is an integer from 12 to 30 and m is an integer from 25 to 61.

7. The helical discotic switch of claim 4, wherein $R_1$, $R_2$, $R_3$ and $R_4$ have the structure $C_nH_m$ wherein n is 12 and m is 25.

8. The helical discotic switch of claim 1, wherein $R_1$, $R_2$, $R_3$ and $R_4$ are alkylaryl.

9. The helical discotic switch of claim 1, wherein $R_5$ is H.

10. The helical discotic switch of claim 1, wherein $R_5$ is substituted or unsubstituted alkyl or aryl.

11. The helical discotic switch of claim 10, wherein $R_5$ is benzyl.

12. The helical discotic switch of claim 1, wherein the electric field is generated by a square electric wave.

13. The helical discotic switch of claim 1, wherein the electric field is generated by a triangular electric wave.

14. The helical discotic switch of claim 13, wherein the triangular electric wave has a peak to peak voltage of at least 20 volts to generate light switching effect.

15. The helical discotic switch of claim 13, wherein the triangular electric wave has a peak to peak voltage between 20 and 2,000 volts to generate light switching effect.

16. The helical discotic switch of claim 13, wherein the triangular electric wave has a peak to peak voltage between 30 and 1,000 volts to generate light switching effect.

17. The helical discotic switch of claim 13, wherein the triangular electric wave has a peak to peak voltage between 60 and 300 volts to generate light switching effect.

18. The helical discotic switch of claim 1, wherein the switching time for light transmission is between 0.0001 and 0.2 seconds; wherein the switching time varies as the square of the voltage of the electric field.

19. The helical discotic switch of claim 18, wherein the switching time for light transmission is between 0.0005 and 0.1 second.

20. The helical discotic switch of claim 18, wherein the switching time for light transmission is between 0.001 and 0.01 second.

21. The helical discotic switch of claim 1, wherein the helicene compound is in an organic solvent at a concentration between 0.1 and 2 molars.

22. A helicene compound having the structure:

wherein X is O, or S and Y is —O—C(=O)CH$_2$—O—R$_5$, wherein $R_5$ is H, substituted or unsubstituted alkyl, alkenyl, cycloalkyl, aryl, or arylalkyl, wherein $R_1$, $R_2$, $R_3$ and $R_4$ are independently the same or different and are substituted or unsubstituted alkyl, alkenyl, cycloalkyl, aryl, or arylalkyl.

23. The helicene compound of claim 22, wherein $R_1$, $R_2$, $R_3$ and $R_4$ are substituted or unsubstituted alkyl or aryl.

24. The helicene compound of claim 22, wherein $R_1$, $R_2$, $R_3$ and $R_4$ are substituted or unsubstituted aryl.

25. The helicene compound of claim 22, wherein $R_1$, $R_2$, $R_3$ and $R_4$ have the structure $C_nH_m$ wherein n is an integer $\geqq 3$ and m is an integer $\leqq 2n+1$.

26. The helicene compound of claim 25, wherein $R_1$, $R_2$, $R_3$ and $R_4$ have the structure $C_nH_m$ wherein n is an integer from 3 to 50 and m is an integer from 7 to 101.

27. The helicene compound of claim 25, wherein $R_1$, $R_2$, $R_3$ and $R_4$ have the structure $C_nH_m$ wherein n is an integer from 12 to 30 and m is an integer from 25 to 61.

28. The helicene compound of claim 25, wherein $R_1$, $R_2$, $R_3$ and $R_4$ have the structure $C_nH_m$ wherein n is 12 and m is 25.

29. The helicene compound of claim 22, wherein $R_1$, $R_2$, $R_3$ and $R_4$ are alkylaryl.

30. The helicene compound of claim 22, wherein $R_5$ is H.

31. The helicene compound of claim 22, wherein $R_5$ is substituted or unsubstituted alkyl or aryl.

32. The helicene compound of claim 22, wherein $R_5$ is benzyl.

33. A liquid crystal having a spiral coil structure and a dipole moment along its axis, comprising the helicene compound of claim 22.

34. A liquid crystal having a spiral coil structure and a dipole moment along its axis, comprising the helicene compound of claim 32.

35. A composition comprising the compound of claim 22 and an organic solvent.

36. The composition of claim 35, wherein the compound is at a concentration of 0.05 to 2.0 molar.

* * * * *